(12) United States Patent
Roy et al.

(10) Patent No.: US 8,469,992 B2
(45) Date of Patent: Jun. 25, 2013

(54) APPARATUS FOR PERFORMING AN ELECTROSURGICAL PROCEDURE

(75) Inventors: Jeffrey M. Roy, Boulder, CO (US); Duane E. Kerr, Loveland, CO (US)

(73) Assignee: Covidien LP, Mansfield, MA (US)

( * ) Notice: Subject to any disclaimer, the term of this patent is extended or adjusted under 35 U.S.C. 154(b) by 460 days.

(21) Appl. No.: 12/792,299

(22) Filed: Jun. 2, 2010

(65) Prior Publication Data
US 2011/0301599 A1 Dec. 8, 2011

(51) Int. Cl.
*A61B 17/29* (2006.01)
*A61B 18/14* (2006.01)

(52) U.S. Cl.
USPC .................................... 606/205; 606/51

(58) Field of Classification Search
USPC ................... 606/45–52, 205–207
See application file for complete search history.

(56) References Cited

U.S. PATENT DOCUMENTS

| | | | |
|---|---|---|---|
| D263,020 S | 2/1982 | Rau, III | |
| 4,509,518 A | 4/1985 | McGarry et al. | |
| 4,624,254 A | 11/1986 | McGarry et al. | |
| D295,893 S | 5/1988 | Sharkany et al. | |
| D295,894 S | 5/1988 | Sharkany et al. | |
| 5,250,056 A | 10/1993 | Hasson | |
| 5,318,589 A * | 6/1994 | Lichtman | 606/205 |
| D348,930 S | 7/1994 | Olson | |
| 5,342,359 A * | 8/1994 | Rydell | 606/51 |
| 5,454,378 A | 10/1995 | Palmer et al. | |
| D384,413 S | 9/1997 | Zlock et al. | |
| 5,683,388 A * | 11/1997 | Slater | 606/51 |
| 5,718,703 A * | 2/1998 | Chin | 606/49 |
| D424,694 S | 5/2000 | Tetzlaff et al. | |
| D425,201 S | 5/2000 | Tetzlaff et al. | |
| D449,886 S | 10/2001 | Tetzlaff et al. | |
| D457,958 S | 5/2002 | Dycus et al. | |
| D457,959 S | 5/2002 | Tetzlaff et al. | |
| 6,533,784 B2 | 3/2003 | Truckai et al. | |
| D493,888 S | 8/2004 | Reschke | |
| 6,770,072 B1 | 8/2004 | Truckai et al. | |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

International Search Report EP11168419.7 dated Aug. 8, 2011.

(Continued)

*Primary Examiner* — Michael Peffley (57) ABSTRACT

An endoscopic forceps is provided. The endoscopic forceps includes a housing having a shaft that extends therefrom and defines a longitudinal axis therethrough. An end effector assembly operatively connects to a distal end of the shaft and has a movable jaw member and a non-movable jaw member. The movable jaw member has a substantially flexible medial portion and is movable relative to the non-movable jaw member from an initial position for positioning tissue therebetween, to a subsequent or clamping position wherein the movable and non-movable jaw members cooperate to grasp tissue therebetween. A drive assembly is operably coupled to the housing and includes a drive wire that operably couples to the movable jaw member. Proximal movement of the drive rod causes the medial portion of the movable jaw member to flex inwardly along a substantial length thereof and toward the non-movable jaw member.

17 Claims, 3 Drawing Sheets

U.S. PATENT DOCUMENTS

| | | | |
|---|---|---|---|
| D496,997 S | 10/2004 | Dycus et al. |
| 6,802,843 B2 | 10/2004 | Truckai et al. |
| D499,181 S | 11/2004 | Dycus et al. |
| D509,297 S | 9/2005 | Wells |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,766,910 B2 | 8/2010 | Hixson |
| 7,887,536 B2 | 2/2011 | Johnson et al. |
| 7,918,848 B2 | 4/2011 | Lau |
| 7,951,150 B2 | 5/2011 | Johnson et al. |
| 8,016,827 B2 | 9/2011 | Chojin |
| 8,112,871 B2 | 2/2012 | Brandt et al. |
| 8,133,254 B2 | 3/2012 | Dumbauld et al. |
| 8,137,273 B2 | 3/2012 | Everett et al. |
| 8,142,473 B2 | 3/2012 | Cunningham |
| 8,162,965 B2 | 4/2012 | Reschke et al. |
| 8,187,273 B2 | 5/2012 | Kerr et al. |
| 8,197,479 B2 | 6/2012 | Olson et al. |
| 8,226,650 B2 | 7/2012 | Kerr |
| 8,251,994 B2 | 8/2012 | McKenna et al. |
| 8,266,783 B2 | 9/2012 | Brandt et al. |
| 8,277,446 B2 | 10/2012 | Heard |
| 8,277,447 B2 | 10/2012 | Garrison et al. |
| 8,282,634 B2 | 10/2012 | Cunningham |
| 8,287,536 B2 | 10/2012 | Mueller et al. |
| 8,292,886 B2 | 10/2012 | Kerr et al. |
| 8,323,310 B2 | 12/2012 | Kingsley |
| 8,343,150 B2 | 1/2013 | Artale |
| 8,343,151 B2 | 1/2013 | Siebrecht et al. |
| 2003/0114851 A1 | 6/2003 | Truckai et al. |
| 2005/0096645 A1 | 5/2005 | Wellman et al. |
| 2006/0217697 A1 | 9/2006 | Lau et al. |
| 2007/0173814 A1 | 7/2007 | Hixson et al. |
| 2007/0260242 A1 | 11/2007 | Dycus et al. |
| 2010/0023009 A1 | 1/2010 | Moses et al. |
| 2010/0087816 A1 | 4/2010 | Roy |
| 2010/0094271 A1 | 4/2010 | Ward et al. |
| 2010/0094287 A1 | 4/2010 | Cunningham et al. |
| 2010/0100122 A1 | 4/2010 | Hinton |
| 2010/0130971 A1 | 5/2010 | Baily et al. |
| 2010/0179543 A1 | 7/2010 | Johnson et al. |
| 2010/0179545 A1 | 7/2010 | Twomey et al. |
| 2010/0179546 A1 | 7/2010 | Cunningham |
| 2010/0249769 A1 | 9/2010 | Nau, Jr. et al. |
| 2010/0280511 A1 | 11/2010 | Rachlin et al. |
| 2011/0034918 A1 | 2/2011 | Reschke |
| 2011/0046623 A1 | 2/2011 | Reschke |
| 2011/0054468 A1 | 3/2011 | Dycus |
| 2011/0054469 A1 | 3/2011 | Kappus et al. |
| 2011/0054471 A1 | 3/2011 | Gerhardt et al. |
| 2011/0054472 A1 | 3/2011 | Romero |
| 2011/0060333 A1 | 3/2011 | Mueller |
| 2011/0060334 A1 | 3/2011 | Brandt et al. |
| 2011/0060335 A1 | 3/2011 | Harper et al. |
| 2011/0071523 A1 | 3/2011 | Dickhans |
| 2011/0077648 A1 | 3/2011 | Lee et al. |
| 2011/0082494 A1 | 4/2011 | Kerr et al. |
| 2011/0098689 A1 | 4/2011 | Nau, Jr. et al. |
| 2011/0118736 A1 | 5/2011 | Harper et al. |
| 2011/0184405 A1 | 7/2011 | Mueller |
| 2011/0190653 A1 | 8/2011 | Harper et al. |
| 2011/0190765 A1 | 8/2011 | Chojin |
| 2011/0193608 A1 | 8/2011 | Krapohl |
| 2011/0218530 A1 | 9/2011 | Reschke |
| 2011/0230880 A1 | 9/2011 | Chojin et al. |
| 2011/0238066 A1 | 9/2011 | Olson |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 20121161 | 4/2002 |
| DE | 10045375 | 10/2002 |
| DE | 20 2007 00931 | 10/2007 |
| DE | 19738457 | 1/2009 |
| EP | 1159926 | 12/2001 |
| EP | 1177771 A1 | 2/2002 |
| EP | 1777771 | 2/2002 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |
| WO | WO2008045348 A2 | 4/2008 |
| WO | WO 2009039179 | 3/2009 |

OTHER PUBLICATIONS

International Search Report EP11168419.7 dated Oct. 11, 2011.
International Search Report EP11168455.1 dated Sep. 26, 2011.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001.

Bergdahl et al. "Studies on Coagulation and the Development of an Automatic Computerized Bipolar Coagulator" J.Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003.

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product,Literature 2000.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.

Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9. dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9. dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.1 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1. dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report Ep 07 021646.0 dated Jul. 9, 2008.

Int'l Search Report Ep 07 021647.8 dated May 2, 2008.
Int'l Search Report Ep 08 002692.5 dated Dec. 12, 2008.
Int'l Search Report Ep 08 004655.0 dated Jun. 24, 2008.
Int'l Search Report Ep 08 006732.5 dated Jul. 29, 2008.
Int'l Search Report Ep 08 006917.2 dated Jul. 3, 2008.
Int'l Search Report Ep 08 016539.2 dated Jan. 8, 2009.
Int'l Search Report Ep 08 020807.7 dated Apr. 24, 2009.
Int'l Search Report Ep 09 003677.3 dated May 4, 2009 •.
Int'l Search Report Ep 09 003813.4 dated Aug. 3, 2009.
Int'l Search Report Ep 09 004491.8 dated Sep. 9, 2009.
Int'l Search Report Ep 09 005051.9 dated Jul. 6, 2009.
Int'l Search Report Ep 09 005575.7 dated Sep. 9, 2009.
Int'l Search Report Ep 09 010521.4 dated Dec. 16, 2009.
Int'l Search Report Ep 09 011745.8 dated Jan. 5, 2010.
Int'l Search Report Ep 09 012629.3 dated Dec. 8, 2009.
Int'l Search Report Ep 09 012687.1 dated Dec. 23, 2009.
Int'l Search Report Ep 09 012688.9 dated Dec. 28, 2009.
Int'l Search Report Ep 09 152267.2 dated Jun. 15, 2009.
Int'l Search Report Ep 09 152898.4 dated Jun. 10, 2009.
Int'l Search Report Ep 09 154850.3 dated Jul. 20, 2009.
Int'l Search Report Ep 09 160476.9 dated Aug. 4, 2009.
Int'l Search Report Ep 09 164903.8 dated Aug. 21, 2009.
Int'l Search Report Ep 09 165753.6 dated Nov. 11, 2009.
Int'l Search .Report Ep 09 168153.6 dated Jan. 14, 2010.
Int'l Search Report Ep 09 168810.1 dated Feb. 2, 2010.
Int'l Search Report Ep 09 172749.5 dated Dec. 4, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Intl Search Report PCT/US01/11420 dated Oct. 16, 2001.
Intl Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Intl Search Report PCT/US03/28534 dated Dec. 19, 2003.
Int'l Search Report PCT/USO4/03436 dated Mar. 3, 2005.
Int'l Search Report PCT/USO4/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Intl Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No: 12169753.6 dated Sep. 14, 2012.
European Search Report for European Application No: 11168458.5 dated Jul. 21, 2011.
U.S. Appl. No. 12/336,970, filed Dec. 17, 2008, Sremcich et al.

* cited by examiner

APPARATUS FOR PERFORMING AN ELECTROSURGICAL PROCEDURE

BACKGROUND

1. Technical Field

The present disclosure relates to an apparatus for performing an electrosurgical procedure. More particularly, the present disclosure relates to an electrosurgical apparatus including an end effector assembly having a pair of jaw members that provide a mechanical advantage at the end effector.

2. Description of Related Art

Electrosurgical instruments, e.g., electrosurgical forceps (open or closed type), are well known in the medical arts and typically include a housing, a handle assembly, a shaft and an end effector assembly attached to a distal end of the shaft. The end effector includes jaw members configured to manipulate tissue (e.g., grasp and seal tissue). Typically, the electrosurgical forceps utilizes both mechanical clamping action and electrical energy to effect hemostasis by heating the tissue and blood vessels to coagulate, cauterize, seal, cut, desiccate, and/or fulgurate tissue. Typically, one or more driving mechanisms, e.g., a drive assembly including a drive rod, is utilized to cooperate with one or more components operatively associated with the end effector to impart movement to one or both of the jaw members.

In certain instances, to facilitate moving the jaw members from an open position for grasping tissue to a closed position for clamping tissue (or vice versa) such that a consistent, uniform tissue effect (e.g., tissue seal) is achieved, one or more types of suitable devices may be operably associated with the electrosurgical forceps. For example, in some instances, one or more types of springs, e.g., a compression spring, may operably couple to the handle assembly associated with the electrosurgical forceps. In this instance, the spring is typically operatively associated with the drive assembly to facilitate actuation of a movable handle associated with the handle assembly to ensure that a specific closure force between the jaw members is maintained within one or more suitable working ranges.

In certain instances, the shaft may bend or deform during the course of an electrosurgical procedure. For example, under certain circumstances, a clinician may intentionally bend or articulate the shaft to gain desired mechanical advantage at the surgical site. Or, under certain circumstances, the surgical environment may cause unintentional or unwanted bending or flexing of the shaft, such as, for example, in the instance where the shaft is a component of a catheter-based electrosurgical forceps. More particularly, shafts associated with catheter-based electrosurgical forceps are typically designed to function with relatively small jaw members, e.g., jaw members that are configured to pass through openings that are 3 mm or less in diameter. Accordingly, the shaft and operative components associated therewith, e.g., a drive rod, are proportioned appropriately. That is, the shaft and drive rod are relatively small.

As can be appreciated, when the shaft is bent or deformed (either intentionally or unintentionally) the frictional losses associated with drive rod translating through the shaft are transferred to the spring in the housing, which, in turn, may diminish, impede and/or prevent effective transfer of the desired closure force that is needed at the jaw members. Moreover, the frictional losses may also lessen the operative life of the spring, which, in turn, ultimately lessens the operative life of the electrosurgical instrument.

An increased mechanical advantage and/or mechanical efficiency with respect to transferring the closure force(s) from the handle assembly to the jaw members may prove advantageous in the relevant art.

SUMMARY

The present disclosure provides an endoscopic forceps. The endoscopic forceps includes a housing having a shaft that extends therefrom and defines a longitudinal axis therethrough. An end effector assembly operatively connects to a distal end of the shaft and has a movable jaw member and a non-movable jaw member. The movable jaw member has a substantially flexible medial portion and is movable relative to the non-movable jaw member from an initial position for positioning tissue therebetween, to a clamping position wherein the movable and non-movable jaw members cooperate to grasp tissue therebetween. A drive assembly is operably coupled to the housing and includes a drive wire that operably couples to the substantially flexible medial portion of the movable jaw member. Proximal movement of the drive rod causes the substantially flexible medial portion movable jaw member to flex inwardly along a substantial length thereof and toward the non-movable jaw member.

The present disclosure provides an endoscopic forceps. The endoscopic forceps includes a housing having a shaft that extends therefrom and defines a longitudinal axis therethrough. An end effector assembly is operatively connected to a distal end of the shaft and has a pair of spaced-apart first and second jaw members. Each of the spaced-apart first and second jaw members includes a respective medial portion. One or both of the medial portions is substantially flexible and movable relative to the other medial portion. The flexible and movable medial portion(s) being movable from an initial position for positioning tissue between the first and second jaw members, to a clamping position wherein the first and second jaw members cooperate to grasp tissue therebetween. A drive assembly is operably coupled to the housing and includes one or more drive wire that operably couples to the jaw member having the substantially flexible and movable medial portion. Proximal movement of the one or more drive wires causes the substantially flexible and movable medial portion to flex inwardly along a substantial length thereof toward the other medial portion.

The present disclosure provides a forceps. The endoscopic forceps includes a housing having a shaft that extends therefrom and defines a longitudinal axis therethrough. An end effector assembly operatively connects to a distal end of the shaft and has a movable jaw member and a non-movable jaw member. The movable jaw member has a substantially flexible medial portion and is movable relative to the non-movable jaw member from an initial position for positioning tissue therebetween, to a clamping position wherein the movable and non-movable jaw members cooperate to grasp tissue therebetween. A drive assembly is operably coupled to the housing and includes a drive wire that operably couples to the substantially flexible medial portion of the movable jaw member. Proximal movement of the drive rod causes the substantially flexible medial portion movable jaw member to flex inwardly along a substantial length thereof and toward the non-movable jaw member.

In embodiments, the forceps may be an open type forceps that is configured for an open surgical procedure.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1A:
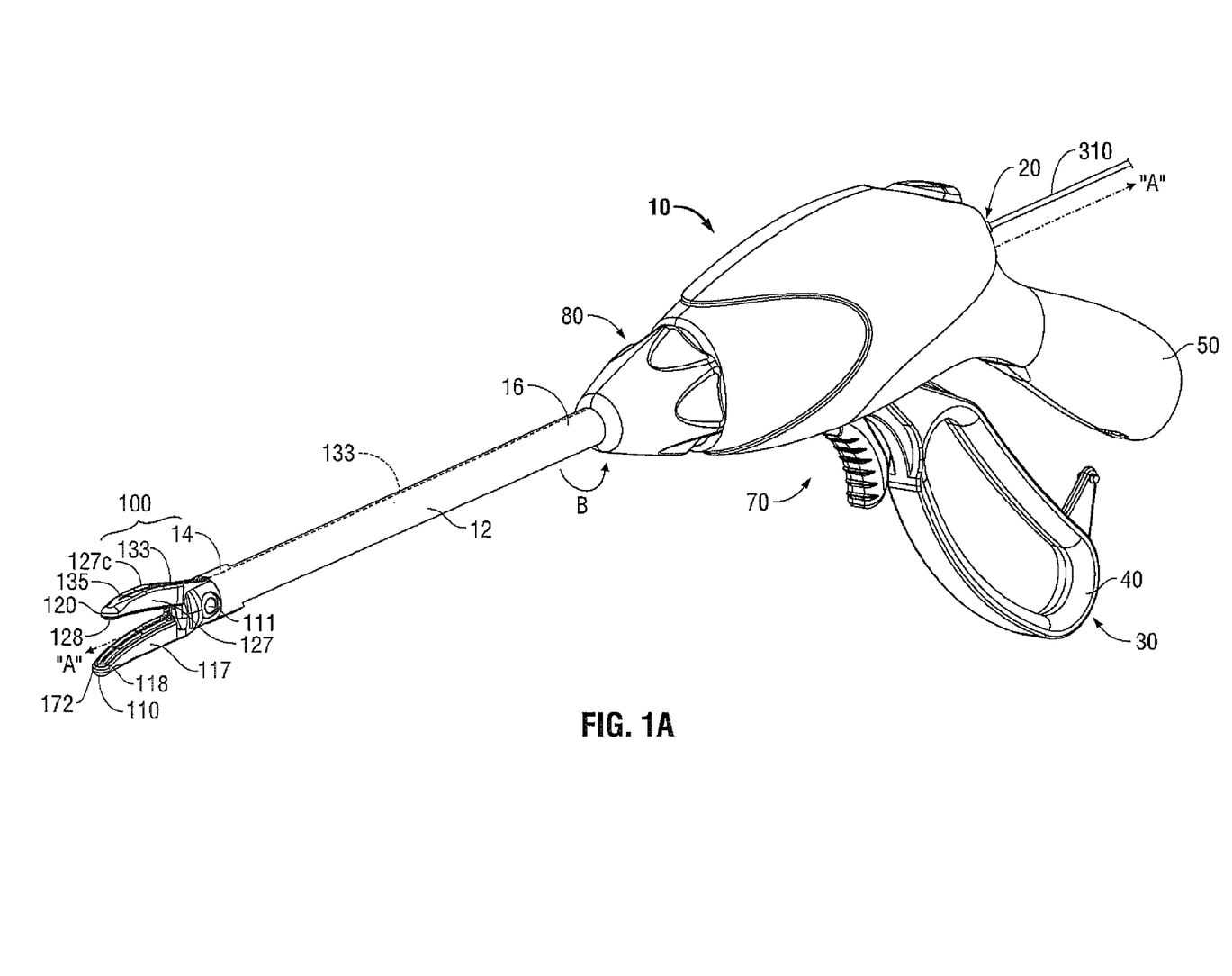
FIG. 1A is a side, perspective view of an endoscopic bipolar forceps showing an end effector assembly including jaw members according to an embodiment of the present disclosure.
Figure 1B:
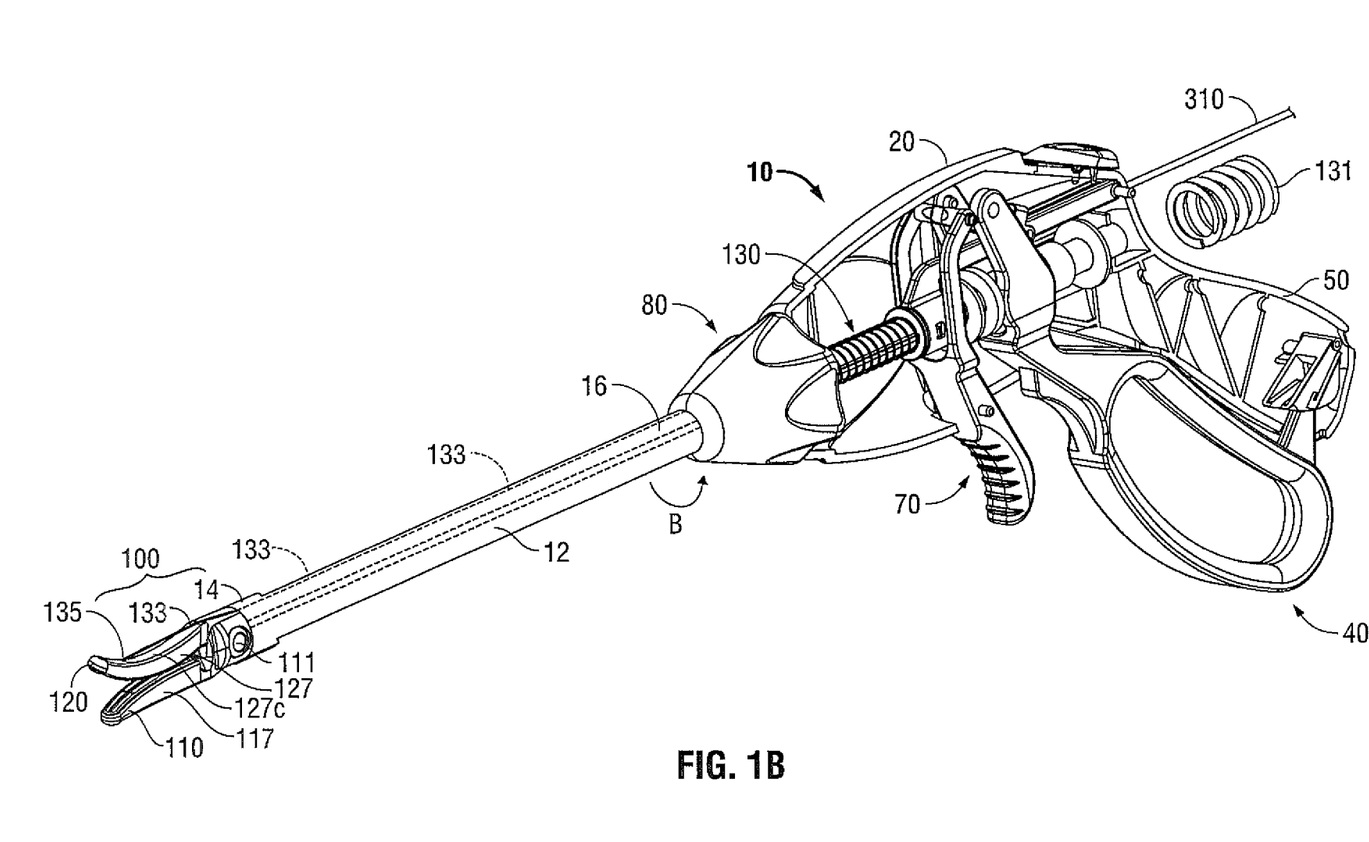
FIG. 1B is a side, perspective view of the endoscopic bipolar forceps depicted in FIG. 1A illustrating internal components thereof and a handle assembly associated with the endoscopic bipolar forceps.

With reference to FIGS. 1A and 1B, an illustrative embodiment of an electrosurgical apparatus, e.g., a bipolar forceps 10 (forceps 10) is shown. Forceps 10 is operatively and selectively coupled to an electrosurgical generator (not shown) for performing an electrosurgical procedure. As noted above, an electrosurgical procedure may include sealing, cutting, cauterizing coagulating, desiccating, and fulgurating tissue all of which may employ RF energy. The electrosurgical generator may be configured for monopolar and/or bipolar modes of operation and may include or be in operative communication with a system (not shown) that may include one or more processors in operative communication with one or more control modules that are executable on the processor. The control module (not explicitly shown) may be configured to instruct one or more modules to transmit electrosurgical energy, which may be in the form of a wave or signal/pulse, via one or more cables (e.g., an electrosurgical cable 310) to the forceps 10.

Forceps 10 is shown configured for use with various electrosurgical procedures and generally includes a housing 20, electrosurgical cable 310 that connects the forceps 10 to the electrosurgical generator, a rotating assembly 80 and a trigger assembly 70. For a more detailed description of the rotating assembly 80, trigger assembly 70, and electrosurgical cable 310 (including line-feed configurations and/or connections), reference is made to commonly-owned U.S. patent application Ser. No. 11/595,194 filed on Nov. 9, 2006, now U.S. Patent Publication No. 2007/0173814.

With continued reference to FIGS. 1A and 113, forceps 10 includes a shaft 12 that has a distal end 14 configured to mechanically engage an end effector assembly 100 operably associated with the forceps 10 and a proximal end 16 that mechanically engages the housing 20. In the drawings and in the descriptions that follow, the term "proximal," as is traditional, will refer to the end of the forceps 10 which is closer to the user, while the term "distal" will refer to the end that is farther from the user.

Handle assembly 30 includes a fixed handle 50 and movable handle 40. In one particular embodiment, fixed handle 50 is integrally associated with housing 20 and handle 40 is movable relative to fixed handle 50 for effecting movement of one or more components, e.g., a drive wire 133, operably associated with a drive assembly 130 (FIG. 1B) via one or more suitable mechanical interfaces, e.g., a linkage interface, gear interface, or combination thereof.

Drive assembly 130 is in operative communication with handle assembly 30 (see FIGS. 1A and 1B) for imparting movement of one or both of a pair of jaw members 110, 120 of end effector assembly 100, described in greater detail below. Conventional drive assemblies typically utilize one or more types of springs, e.g., a compression spring, to facilitate closing the jaw members 110 and 120. For illustrative purposes, a compression spring 131 (see FIG. 1B) is shown separated from the housing 20. In accordance with the present disclosure, the drive assembly 130 includes drive wire 133 that operably couples to one or both of the jaw members 110 and 120, wherein one or both of the jaw members 110 and 120 includes a substantially flexible medial portion, e.g., a medial portion 117c. Medial portion 117c functions to facilitate closing the jaw members 110 and 120 and, thus, may eliminate the need for the compression spring 131.

Drive wire 133 is configured such that proximal movement thereof causes the movable jaw member, e.g., jaw member 120, and operative components associated therewith, e.g., a seal plate 128, to "flex" or "bend" inwardly substantially across a length thereof toward the non-movable jaw member, e.g., jaw member 110. Moreover, drive wire 133 is configured such that this "flexing" or "bending" does not cause permanent damage to the jaw member 110 or jaw housing 117, i.e., the jaw member 110 may return to its original or "unloaded" state. With this purpose in mind, drive rod or wire 133 may be made from any suitable material and is proportioned to translate within the shaft 12. In the illustrated embodiments, drive wire 133 extends through the shaft 12 past the distal end 14, see FIGS. 1A and 2A, for example. In an initial position, i.e., jaw member 120 is in a "non-flexed" condition, a proximal portion of the drive wire 133 is disposed in a parallel orientation with respect to a longitudinal axis "B-B" that is parallel to the longitudinal axis "A-A," and a distal portion of the drive wire 133 is disposed in a generally oblique orientation with respect to the longitudinal axis "B-B" and/or "A-A," see FIG. 2A. In a subsequent position, i.e., jaw member 120 is in a "flexed" condition, the proximal portion, as does the distal portion, of the drive wire 133 is disposed in a parallel orientation with respect to a longitudinal axis "B-B" and/or "A-A," see FIG. 2B.

Drive wire 133 is operably disposed adjacent a proximal surface 127d of the jaw housing 127. Disposing the drive wire 133 adjacent the proximal surface 127d of the jaw housing 127 facilitates transferring the load or force that is provided by the drive wire 133 to move, e.g., "flex" or "bend," the jaw member 120, or portion thereof. More particularly, the load or force generates a "snapping" action that is designed to "flex" or "bend" the jaw member 120 into the closed or clamping position when the drive wire 133 is moved proximally. Additionally, disposing the drive wire 133 adjacent the proximal surface 127d allows the jaw member 120 to "flex" or "bend" with minimal or no interference from the drive wire 133. Drive wire 133 is operably coupled to the movable jaw member, e.g., jaw member 120. More particularly, a distal end 135 of the drive wire 133 operably couples, by any suitable coupling methods, to a distal end 127a of a jaw housing 127 of the movable jaw member 120 (see FIG. 2A). In the illustrated embodiment, distal end 135 operably couples to distal end 127a via one of soldering, brazing, welding and a mechanical interlock system.

Figure 2A:
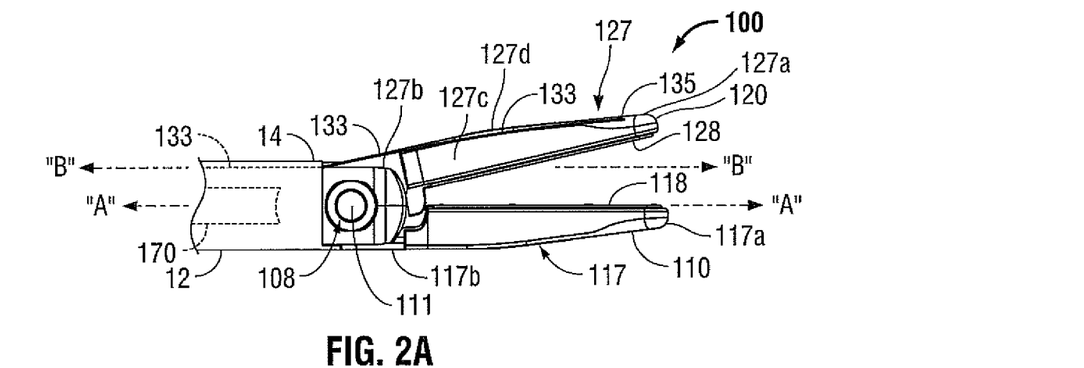
FIGS. 2A and 2B are schematic views of the jaw members depicted in FIGS. 1A and 1B.
Figure 2B:
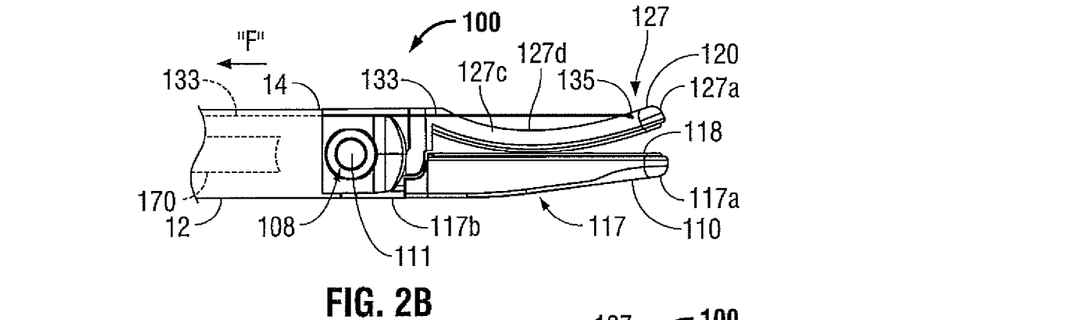

Referring now to FIGS. 2A and 2B, end effector assembly 100 is illustrated operably disposed at the distal end 14 of the shaft 12. More particularly, end effector assembly 100 includes opposing jaw members 110 and 120 that are operatively and pivotably coupled to each other and located adjacent the distal end 14 of shaft 12. More particularly, respective proximal ends 117b and 127b of jaw members 110 and 120 are operably secured to the distal end 14 of the shaft 12.

Jaw member 110 includes an electrically conductive sealing plate 118 that is operably supported on and secured to a distal end 117a of jaw housing 117. Likewise, jaw member 120 includes an electrically conductive sealing plate 128 that is operably supported on and secured to a distal end 127a of jaw housings 127. Each of the sealing plates 118, 128 is formed from a sheet of conductive metal, e.g., surgical steel, of suitable proportion.

Jaw members 110 and 120 are configured to mutually cooperate to grasp, seal and, in some cases, divide large tubular vessels and large vascular tissues. With this purpose in mind, and in the embodiment illustrated in FIGS. 2A and 2B, one of the jaw members is movable and one of jaw members is non-movable or stationary. For illustrative purposes, jaw member 120 is described as being movable, i.e. jaw member 120 (or portion thereof) is configured to "flex" or "bend" toward jaw member 110, and jaw member 110 is described as being stationary.

In certain instances, the drive wire 133 may be resilient and dimensioned to "bend" or "flex" toward proximal surface 127d of the jaw housing 127. In this instance, the drive wire 133 may be configured to contact the proximal surface 127d when the drive wire 133 is moved proximally. As can be appreciated, this contact between the drive wire 133 and the proximal surface 127d facilitates moving, e.g., "bending" or "flexing," the jaw housing 127, and, thus, "bending" or "flexing," seal plate 128 that is operably secured to the jaw housing 127 toward a seal plate 118 that is operably secured to the jaw housing 117 of the jaw member 110.

With continued reference to FIGS. 2A and 2B, jaw member 120 including jaw housing 127 may be formed from any suitable material, including but not limited to metal, metal alloys, plastic, plastic composites, or combinations thereof. In the illustrated embodiment, jaw housing 127 is formed from a metal (and/or plastic) that provides a degree of flexibility when a load or force of suitable proportion, e.g., load or force provided by the drive wire 133 when the drive wire 133 is moved proximally, is applied to jaw member 120.

As noted above, jaw member 120, or portion thereof, moves with respect to the shaft 12 and/or jaw member 110. More particularly, a medial portion 127c including seal plate 128 associated with the jaw member 120 is configured to "flex" or "bend" inward and toward the seal plate 118 of jaw member 110 when the drive wire 133 is moved a predetermined distance proximally from its initial position. That is, as the drive wire 133 is moved in a proximal direction, a downward force, e.g., a force normal to the proximal surface 127d, is developed on the medial portion 127c. This downward force causes the medial portion 127c to "flex" or "bend" inward and toward the seal plate 118 of jaw member 110. Likewise, the medial portion 127c is configured to "flex" or "bend" outward and away from the seal plate 118 of jaw member 110 when the drive wire 133 moves distally and back to its initial position. That is, when the downward force is not acting on the proximal surface 127d.

To facilitate "flexing" or "bending" of jaw housing 127 (or portion thereof, e.g., medial portion 127c), jaw housing 127 is substantially resilient or "spring-like." In the illustrated embodiment, the medial portion 127c of the jaw housing 127 is substantially resilient, while the proximal and distal ends 127a and 127b, respectively, are substantially rigid. This configuration of a substantially resilient medial portion 127c and substantially rigid respective proximal and distal ends 127a and 127b facilitates "flexing" or "bending" the medial portion 127c. That is, when the drive wire 133 is moved proximally, the medial portion 127c and, thus, the seal plate 128, "snaps" toward the seal plate 118 of the jaw member 110 and locks into a closed or clamped position. This "snapping" and locking action facilitates grasping and, subsequently, sealing tissue. Moreover, when the medial portion 127c of the jaw housing 127 and seal plate 128 is "snapped" and locked into a clamped position, a closure or sealing force, e.g., a closure force in the range of about 3 kg/cm$^2$ to about 16 kg/cm$^2$, is provided between the jaw members 110 and 120 for sealing tissue.

Unlike jaw member 120, jaw member 110 is stationary or non-movable. That is, jaw member 110, and operative components associated therewith, e.g., a medial portion 117c and seal plate 118, do not move with respect to the shaft 12 and/or jaw member 120. In this regard, the jaw housing 117 and, thus, the seal plate 118 are substantially rigid. The rigidity of the jaw housing 117 and seal plate 118 provides a substantially rigid surface that together with the medial portion 127c of jaw housing 127 and seal plate 128 facilitates grasping tissue after tissue is positioned between the jaw members 110 and 120 and the drive wire 133 is moved proximally. Accordingly, jaw member 110 is formed from a metal (and/or plastic) that provides a degree of rigidity that is capable of maintaining jaw member 110 in a substantially fixed position when a force of suitable proportion, e.g., force provided by the drive wire 133 when the drive wire 133 is move proximally, is applied to the jaw member 120 and the jaw member 120 is caused to move, e.g., "flex" or "bend," inwardly and toward the jaw member 110.

The jaw members 110 and 120 may be coupled to each other via any suitable coupling methods. In the illustrated embodiment, an opening 108 is defined in and extends through the each of the jaw housings 117 and 127 and is configured to receive a pivot pin 111. Opening 108 is shown engaged with pivot pin 111 and as such is not explicitly visible. Pivot pin 111 facilitates "flexing" or "bending" of the medial portion 127c including seal plate 128 when the drive wire 133 is moved proximally and/or distally.

In an assembled configuration pivot pin 111 is positioned within the openings associated with each of the jaw members 110 and 120. Once assembled, the jaw members 110 and 120 may be pivotably supported at the distal end 14 of the shaft 12 by known methods, such as, for example, by the method described in commonly-owned U.S. Patent Application publication No. 2007/0260242, filed Jul. 11, 2007.

In use, initially jaw members 110 and 120 are positioned in an open configuration (FIGS. 1A and 2A). Tissue is positioned between the jaw members 110 and 120. Movable handle 40 is moved proximally (FIG. 1B), which, in turn, causes the drive wire 133 to move proximally in the direction indicated by directional arrow "F" (FIG. 2B). Proximal movement of the drive wire 133 causes the "snapping" action of medial portion 127c of the jaw housing 127, and the seal plate 128 to "flex" or "bend" inward toward medial portion 117c including the seal plate 118 of the jaw member 110 such that tissue is grasped between the jaw members 110 and 120 (FIG. 2B). Subsequently, electrosurgical energy is transmitted to the seal plates 118 and 128 such that an electrosurgical effect, e.g., tissue seal, is achieved at tissue. The drive wire 133 and flexible medial portion 127c associated with the jaw member 120 provides an additional mechanical advantage at the jaw members 110 and 120 and reduces the frictional losses that are typically associated with conventional forceps when a drive rod is translated within a shaft to make the necessary closure force to seal tissue, e.g., the closure force is offloaded and/or diminished by the drive wire 133 and flexible medial portion 127c.

From the foregoing and with reference to the various figure drawings, those skilled in the art will appreciate that certain modifications can also be made to the present disclosure without departing from the scope of the same. For example, in certain embodiments (FIGS. 3A and 3B), it may prove useful to have both the jaw members 110 and 120 be movable with respect to one another. In this instance, jaw housing 117 of jaw member 110 includes a seal plate 118 and corresponding medial portion 117c that are collectively configured to function similarly to that of seal plate 128 and medial portion 127c of jaw housing 127.

Figure 3A:
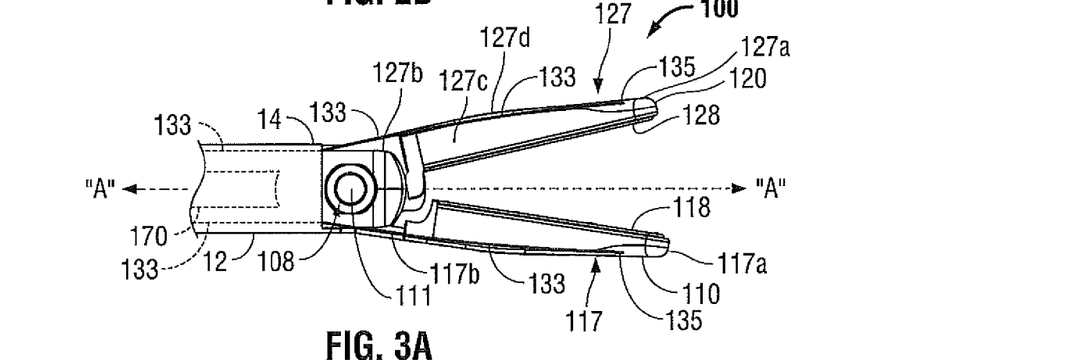
FIGS. 3A and 3B are schematic views of an alternate embodiment of the jaw members depicted in FIGS. 2A and 2B.
Figure 3B:
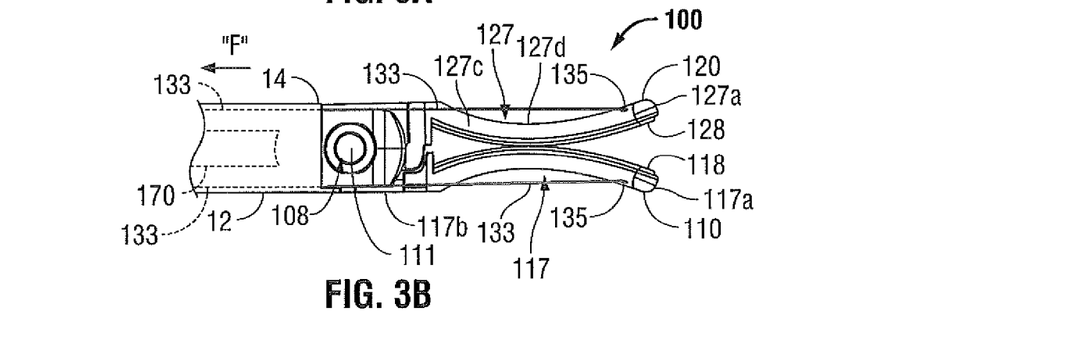

In the embodiment illustrated in FIGS. 3A and 3B, two drive wires 133 may operably couple to a respective distal ends 117a and 127a of jaw housings 117 and 127.

Operation of the forceps 10 that includes jaw members 110 and 120 configured in a manner illustrated in FIGS. 3A and 3B is substantially similar that as previously described above with respect to FIGS. 2A and 2B. A distinguishing feature of the operation of the forceps 10 with the jaw members depicted in FIGS. 3A and 3B when compared to the operation of the forceps 10 with the jaw members depicted in FIGS. 2A and 2B, is that both of the medial portions 117c and 127c of respective jaw housing 117 and 127 provide a "snapping" action, and "flex" or "bend" when the respective drive wires 133 are moved proximally.

It is contemplated that one or more cutting elements 170 may be operably associated with the forceps 10 and configured to sever tissue after tissue has been surgically treated, e.g., sealed. In this instance, the cutting element 170 is configured to translate within a pair of cutting or knife channels 172 (FIG. 1A) defined within the jaw members 110 and 120. For a more detailed description of a cutting element that may be utilized with the forceps 10, reference is again made to commonly-owned U.S. Patent Publication No. 2007/0173814.

Cutting element may be utilized to function in a manner as described in U.S. Patent Publication No, 2007/0173814. In addition, cutting element may be utilized and configured to move or assist in moving the medial portion 127c of the jaw member 120 (or in some instances, medial portion 117c of jaw member 110) back to the initial or "non-flexed" condition. More particularly, during distal translation, a top surface of the cutting element 170 may be configured to contact an interior surface adjacent the medial portion 127c of the jaw member 120. In this instance, when the top surface of the cutting element contacts the interior surface adjacent the medial portion 127c, the medial portion 127c and, thus, the jaw member 120 is moves back to the initial or non-flexed position.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic forceps, comprising:
    a housing having a shaft that extends therefrom and defines a longitudinal axis therethrough; an end effector assembly operatively connected to a distal end of the shaft and having a movable jaw member and a non-movable jaw member, the movable jaw member having a substantially flexible medial portion and movable relative to the non-movable jaw member from an initial position for positioning tissue therebetween, to a clamping position wherein the movable and non-movable jaw members cooperate to grasp tissue therebetween; and
    a drive assembly operably coupled to the housing and including a drive wire that operably couples to the movable jaw member, wherein proximal movement of the drive wire causes the medial portion of the movable jaw member to flex inwardly along a substantial length thereof and toward the non-movable jaw member.

2. An endoscopic forceps according to claim 1, wherein the medial portion of the movable jaw member generates a closure force between the movable and non-movable jaw members that is in the range of about 3 kg/cm.sup.2 to about 16 kg/cm.sup.2 when the movable jaw member is actuated to the clamping position.

3. An endoscopic forceps according to claim 1, wherein the drive wire is substantially flexible along a length thereof.

4. An endoscopic forceps according to claim 1, wherein the drive wire is operably disposed within the shaft and extends along a length thereof.

5. An endoscopic forceps according to claim 1, wherein the drive wire is operably disposed outside the shaft and extends along a length thereof.

6. An endoscopic forceps according to claim 1, wherein the drive wire is operably coupled to the movable jaw member via one of soldering, brazing, welding and a mechanical interlock system.

7. An endoscopic forceps according to claim 1, wherein the drive wire is operably coupled to a movable handle associated with the endoscopic forceps, the movable handle configured such that proximal movement thereof causes the drive wire to move proximally and the medial portion of the movable jaw member to flex inwardly along a substantial length thereof toward the non-movable jaw member.

8. An endoscopic forceps according to claim 1, wherein the drive wire operably couples to a distal end of the movable jaw member.

9. An endoscopic forceps according to claim 1, further including a cutting element that is operably associated with the movable and non-movable jaw members and configured for translation therethrough for severing tissue.

10. An endoscopic forceps according to claim 9, wherein distal translation of the cutting element through the movable and non-movable jaw members causes the movable jaw member to return to the initial position.

11. An endoscopic forceps, comprising:
    a housing having a shaft that extends therefrom and defines a longitudinal axis therethrough;
    an end effector assembly operatively connected to a distal end of the shaft and having a pair of spaced-apart first and second jaw members, each of the spaced-apart first and second jaw members having respective medial portions, at least one of the medial portions being substantially flexible and movable relative to the other medial portion, the substantially flexible and movable medial portion movable from an initial position for positioning tissue between the first and second jaw members, to a clamping position wherein the first and second jaw members cooperate to grasp tissue therebetween; and
    a drive assembly operably coupled to the housing and including at least one drive wire that operably couples to the jaw member having the substantially flexible and movable medial portion, wherein proximal movement of the at least one drive wire causes the substantially flexible and movable medial portion to flex inwardly along a substantial length thereof toward the other medial portion, wherein each of the first and second jaw members includes a respective medial portion substantially flexible and movable relative to each other from an initial position for positioning tissue between the first and second jaw members, to a subsequent position wherein the first and second jaw members cooperate to grasp tissue therebetween, wherein each of the medial portions associated with the one of the first and second jaw members provides a closure force between the jaw members in the range of about 3 kg/cm$^2$ to about 16 kg/cm$^2$ when the first and second jaw members are in the clamping position, and wherein the drive assembly includes at least two drive wires, a first drive wire that operably couples to a distal end of the first jaw member and a second drive wire that operably couples to a distal end of the second jaw member.

12. An endoscopic forceps according to claim 11, wherein each of the at least two drive wires is substantially flexible along a length thereof and is operably disposed within the shaft extending along a length thereof.

13. An endoscopic forceps according to claim 12, wherein each of the at least two drive wires is operably coupled to a respective one of the first and second jaw members via one of soldering, brazing, welding and a mechanical interlock system.

14. An endoscopic forceps according to claim 13, wherein each of the at least two drive wires is operably coupled to a movable handle associated with the endoscopic forceps, the movable handle configured such that proximal movement thereof causes each of the at least two drive wires to move proximally and the medial portions associated with the respective one of the first and second jaw members to flex along a substantial length thereof toward each other.

15. An endoscopic forceps according to claim 14, further including a cutting element that is operably associated with the first and second jaw members and configured for translation therethrough for severing tissue.

16. An endoscopic forceps according to claim 15, wherein distal translation of the cutting element through the first and second jaw members causes each of the medial portions associated with the one of the first and second jaw members to return to their initial position.

17. A forceps, comprising:
a housing having a shaft that extends therefrom and defines a longitudinal axis therethrough;
an end effector assembly operatively connected to a distal end of the shaft and having a movable jaw member and a non-movable jaw member, the movable jaw member having a substantially flexible medial portion and movable relative to the non-movable jaw member from an initial position for positioning tissue therebetween, to a clamping position wherein the movable and non-movable jaw members cooperate to grasp tissue therebetween; and
a drive assembly operably coupled to the housing and including a drive wire that operably couples to the movable jaw member, wherein proximal movement of the drive wire causes the medial portion of the movable jaw member to flex inwardly along a substantial length thereof and toward the non-movable jaw member.

* * * * *